United States Patent
Yan

(10) Patent No.: US 9,939,355 B2
(45) Date of Patent: Apr. 10, 2018

(54) COMPOSITION OF DETECTION AGENTS FOR EPITHELIAL TUMOUR CELLS AND PREPARATION METHOD THEREFOR

(71) Applicant: Wenguang Yan, Xi'an (CN)

(72) Inventor: Wenguang Yan, Xi'an (CN)

( * ) Notice: Subject to any disclaimer, the term of this patent is extended or adjusted under 35 U.S.C. 154(b) by 5 days.

(21) Appl. No.: 14/369,460

(22) PCT Filed: Dec. 28, 2012

(86) PCT No.: PCT/CN2012/087880
§ 371 (c)(1),
(2) Date: Jun. 27, 2014

(87) PCT Pub. No.: WO2013/097771
PCT Pub. Date: Jul. 4, 2013

(65) Prior Publication Data
US 2014/0377796 A1 Dec. 25, 2014

(30) Foreign Application Priority Data
Dec. 29, 2011 (CN) .......................... 2011 1 0449270

(51) Int. Cl.
C12Q 1/04 (2006.01)
G01N 1/30 (2006.01)
G01N 33/50 (2006.01)
A61K 49/00 (2006.01)
G01N 33/52 (2006.01)

(52) U.S. Cl.
CPC ............. *G01N 1/30* (2013.01); *A61K 49/006* (2013.01); *G01N 33/5005* (2013.01); *G01N 33/52* (2013.01); *G01N 2001/302* (2013.01); *G01N 2800/7028* (2013.01)

(58) Field of Classification Search
None
See application file for complete search history.

(56) References Cited

U.S. PATENT DOCUMENTS

2008/0187901 A1* 8/2008 Doorschodt ......... A01N 1/0226
435/1.2
2011/0117549 A1 5/2011 Miyamoto et al.

FOREIGN PATENT DOCUMENTS

CN 101261279 A 9/2008
WO 2010106997 A1 9/2010

OTHER PUBLICATIONS

Deak, "Handbook of Food Spoilage Yeasts", CRC Press, 2007, pp. 281 and 283.*
Innis et al., PCR Protocols: A Guide to Methods and Applications, Academic Press, p. 147, 1990.*
Korea Patent Office, "Office Action for KR 10-2014-7021072," dated Apr. 16, 2015.
Australia Patent Office, "Patent Examination Report for AU 2012361342," dated Jun. 1, 2015.
Reddy, Ja et al., "Folate-targeted, cationic liposome-mediated gene transfer into disseminated peritoneal tumors," Gene Therapy, 2002, p. 1542-1550, vol. 9, Nature Publishing Group.
China Patent Office, "Second Office Action for CN 201110449270.7," dated Jan. 28, 2015.
Europe Patent Office, "Search Report for EP 12861189.4," dated Jun. 17, 2015.
Japan Patent Office, "Office Action for JP 2014-547705," dated Jul. 7, 2015.
Takeo, K. et al., "Separation of monoclonal antibodies from antihapten antisera by two-dimensional affinity electrophoresis," Journal of Chromatography, 1992, p. 365-376, vol. 597, No. 1-2, Elsevier Science Publishers B.V.
Lee, R. et al., "Delivery of Liposomes into Cultured KB Cells via Folate Receptor-mediated Endocytosis," The Journal of Biological Chemistry,1994, p. 3198-3204, vol. 269, No. 5, The American Society for Biochemistry and Molecular Biology, Inc.
Hashizume, M. et al. , "Two cases of ectopic mediastinal parathyroid tumor," The Japanese Association for Chest Surgery, 2006, p. 44-48, NIT-Electronic Library Service.
PCT, "International Search Report for PCT/CN2012/087880," dated Apr. 11, 2013.
PCT, "International Preliminary Report on Patentability for PCT/CN2012/087880," dated Jul. 10, 2014.
PCT, "Notification of Transmittal of the International Search Report and the Written Opinion of the International Searching Authority, or the Declaration," dated Apr. 11, 2013.
China Patent Office, "First Office Action for CN 201110449270.7," dated Jul. 29, 2014.
Zhao, X. B. et al., "Tumor-selective targeted delivery of genes and antisense oligodeoxyribonucleotides via the folate receptor," Advanced Drug Delivery Reviews, 2004, p. 1193-1204, vol. 56, Elsevier B.V.
Canto, M. et al., "Methylene blue-directed biopsies improve detection of intestinal metaplasia and dysplasia in Barrett's esophagus," Gastrointestinal Endoscopy, 2000, p. 560-568, vol. 51, No. 5.

(Continued)

*Primary Examiner* — Erin M Bowers
(74) *Attorney, Agent, or Firm* — Manabu Kanesaka

(57) ABSTRACT

Provided is a composition of detection agents for living cells, especially epithelial tumor cells; the composition contains 0-5% folic acid, 0-10% folic acid complex, 0.01-5% methylene blue, 0.1-10% carbohydrate reducing agent, 2-6% acetic acid, and 3-95% water. Also provided is a preparation method for the composition of detection agents and kits containing the composition of detection agents.

28 Claims, No Drawings

(56) References Cited

OTHER PUBLICATIONS

Guelrud, M. et al., "Acetic acid improves identification of remnant islands of Barrett's epithelium after endoscopic therapy," Gastrointestinal Endoscopy, 1998, p. 512-515, vol. 47, No. 6, New Methods and Materials.

Sega, E. et al., "Tumor detection using folate receptor-targeted imaging agents," Cancer Metastasis Rev., 2008, p. 655-664, Springer Science+Business Media, LLC.

Youlin, Q. et al., "Screen, early diagnosis, and early treatment solutions for cervical cancer," 2003.

Mashberg, A., "Final evaluation of tolonium chloride rinse for screening of high-risk patients with asymptomatic squamous carcinoma," Journal of the American Dental Association, 1983, p. 319-323, vol. 106.

Reddy, J. A. et al., "Targeting Therapeutic and Imaging Agents to Folate Receptor Positive Tumors," Current Pharmaceutical Biotechnology, 2005, p. 131-150, vol. 6, Bentham Science Publishers Ltd.

Chenheng, W. et al., "The alterations of redox status, antioxidative capability of malignant tumors and its association with apoptosis," 2005.

Link, E. M. et al., "Early detection of melanoma metastases with radioiodinated methylene blue," European Journal of Nuclear Medicine, 1998, p. 1322-1329, vol. 25, No. 9, Springer-Verlag.

Leamon, C. et al., "Folate-mediated drug delivery: Effect of Alternative Conjugation Chemistry," Journal of Drug Targeting, 1999, p. 157-169, vol. 7, No. 3, Rights Link.

Leamon, C. et al., "Folate-Liposome-Mediated Antisense Oligodeoxynucleotide Targeting to Cancer Cells: Evaluation in Vitro and in Vivo," Bioconjugate Chem., 2003, p. 738-747, vol. 14, American Chemical Society.

Zhou, Zeng-Tong et al., "The Evaluation of Toluidine Blue Stain in Vivo for Detecting Oral Musosa Premalignant Lesions," J Clin Stomatol, Feb. 2001, p. 52-53, vol. 17, No. 1.

Indonesia Patent Office, "Office Action for Indonesian Patent Application No. P00201404017," dated Dec. 21, 2016.

Vietnam Patent Office, "Office Action for Vietnamese Patent Application No. 1-2014-02545," dated Dec. 28, 2016.

India Patent Office, "Office Action for Indian Patent Application No. 6266/DELNP/2014," dated Dec. 12, 2017.

\* cited by examiner

COMPOSITION OF DETECTION AGENTS FOR EPITHELIAL TUMOUR CELLS AND PREPARATION METHOD THEREFOR

RELATED APPLICATIONS

The present application is National Phase of International Application No. PCT/CN2012/087880 filed Dec. 28, 2012, and claims priority from Chinese Application No. 201110449270.7 filed Dec. 29, 2011.

FIELD OF THE INVENTION

The invention relates to a detecting agent composition, especially to a detecting agent composition for epithelial tumor cells based on color change. The invention further relates to a method for preparing the detecting agent composition, and a kit comprising the detecting agent composition.

BACKGROUND ARTS

Currently, methods for vital staining of human epithelial tumor cells primarily include methods based on acetowhite test, iodine test, toluidine blue test, methylene blue staining, hematoxylin staining and the like.

Specifically, the acetowhite test is to smear acetic acid solution, for example, 3~5% acetic acid solution, on the cervical/vaginal epithelial tissue, and observe whether there is any acetowhite responsive region in the smeared epithelial tissue after waiting for some time. If there is any acetowhite region, this epithelial tissue is suspected to contain tumor cells. However, although this method has high sensitivity, its specificity is poor, that is because besides tumor cells, some inflammatory cells can also generate acetowhiteness, thereby producing false positive results. Moreover, the specificity of this method is heavily affected by the operator's skill level and experience.

The mechanism of the iodine test is reaction with glycogen. It involves smearing Lugol's iodine on cervical epithelial tissues and detecting by observing the iodine staining of the epithelial cells, in which normal epithelium exhibits red-brown or black, whereas abnormal epithelium exhibits thick mustard yellow or yellowish brown. However, if there is epithelial inflammation, these regions may not be stained by iodine, or exhibit colorless loading. Therefore, iodine test has poor specificity on the staining of the epithelial cells[1].

Methods using toluidine blue may cause the staining of the nuclear debris of neutrophils and bacterial, resulting in high false positive rate. It is also difficult to stain cancer and leukoplakia with surface keratinization, which tends to cause false negative[2].

After staining of epithelial tissues with hematoxylin, a high power microscope is needed for observation with complicated operation and high requirements on the expertise and experience of the operator, as well as long inspection time.

The affinity between methylene blue and cancer cells makes malignant tissues prone to blue staining. It is reported that using it for in situ biopsy sampling of esophageal epithelial tissues has the effect of improving positive rate of biopsy[3]. However, there is no report in the art to combine the redox color change reaction of methylene blue with folic acid or folic acid complex so as to rapidly locate and detect epithelial tumor cells by staining and color change reaction.

A composition for detecting epithelial tumor cells, especially, for cervical/vaginal epithelial tissue tumor cells by staining and color change which has high sensitivity, high specificity and simple and rapid operation is urgently needed in the art.

SUMMARY OF THE INVENTION

The inventor of the invention has found that abnormal epithelial tissues can be rapidly and accurately stained specifically by binding of folic acid and/or folic acid complex with excessively expressed folic acid receptor in tumor cells, endocytosis, and color change of methylene blue in redox reaction with reduction state methylene blue participating in the redox system of the tumor cells, thereby distinguishing them from normal tissues, and by color change of the composition of the invention whether the tested tissue cells are tumor cells are rapidly shown, thereby providing rapid, simple, accurate and sensitive location and detection of abnormal epithelial tissues, thereby completing the invention. The detecting agent composition of the invention has high sensitivity, high specificity, simple operation and short inspection time, and the operator does not need technical training. In addition, methylene blue, as an agent widely used clinically, has the advantage of being effective, safe, cheap and easily obtainable, thereby enabling the composition and method of the invention to have these advantages, too.

Therefore, the invention provides a detecting agent composition comprising the following components (by weight percentage):

| | |
|---|---|
| Folic acid | 0-5% |
| Folic acid complexes | 0-10% |
| Methylene blue | 0.01-5% |
| Carbohydrate reducing agent | 0.1-10% |
| Acetic acid | 2-6% |
| Water | 3-95% |

In a preferred embodiment of the aforesaid detecting agent composition, the amount of folic acid is preferably 0-4.5%, more preferably 0-1%.

In another preferred embodiment, the amount of folic acid complex is preferably 0-8%, more preferably 0-1%.

In yet another preferred embodiment, the amount of methylene blue is preferably 0.05-4.5%, more preferably 0.05-0.5%.

In yet another preferred embodiment, the amount of acetic acid is preferably 3-5%.

The carbohydrate reducing agent used in the detecting agent composition of the invention includes various carbohydrates and derivatives thereof, preferably glucose, fructose, galactose, hexose, lactose, maltose, and derivatives thereof, and the like.

Another aspect of the invention relates to a method for preparing the detecting agent of the invention, comprising or consisting of the following steps in order:

(a) dissolving folic acid and/or folic acid complex into a aqueous solvent by the aforesaid weight percentage to form a solution, (b) adding, agitating and dissolving methyelene blue into the solution (a) by the aforesaid weight percentage, (c) adding the carbohydrate reducing agent into the solution (b) by the aforesaid weight percentage, (d) agitating the solution obtained in step (c) for 30 minutes, (e) adding, agitating and dissolving acetic acid into the solution (d) by the aforesaid weight percentage, and the aforesaid steps are all conducted under normal temperature and pressure.

In a preferred aspect, the detecting agent of the invention or the detecting agent prepared by the method of the invention is used for the detection of epithelial tumor cells.

The invention further relates to a method for detecting the lesion of an epithelial tissue comprising:

(a) applying the vital cell detecting agents of the invention to the surface of the epithelial tissue of the subject by a carrier;

(b) observing the color change on the carrier; and (c) determining whether there is lesion in the tested epithelial tissue by color change.

In a preferred embodiment, the method for detecting the lesion of an epithelial tissue further comprises:

(d) observing whether acetowhite response is generated in the surface region of the epithelial tissue to which the vital cell detecting agent of the invention is applied.

In a preferred embodiment, in the method for detecting the lesion of an epithelial tissue according to the invention, the observation in step (b) is made visually.

In a preferred embodiment, in the method for detecting the lesion of an epithelial tissue according to the invention, the observation and determination in steps (b) and (c) are conducted based on the following standards: no color change of the carrier, indicating no lesion of the epithelial tissue; the carrier turning into light bluish green, indicating no abnormal lesion of the epithelial tissue; the carrier turning into dark bluish green/blackish green/purple black, indicating abnormal lesion of the epithelial tissue. Furthermore, if the carrier turns into blackish green/purple black, the region in the epithelial tissue generating acetowhite response can be sampled via biopsy for pathological examination with the patient's consent if the follow-up of the patient cannot be ensured.

In a preferred embodiment, the abnormal lesion is a neoplasia (≥CIN II) and carcinogenesis inside an epithelial tissue.

The detecting agent composition for epithelial tumor cells of the invention can be administered using different ways. The ways of administration include, but are not limited to, smearing. The administration can be performed using a carrier which includes, but is not limited to absorbent cotton swabs, gauze, microcapsules, cellulose membranes, filter paper, nanomaterials, aerogel, and the like.

The detecting agent composition for epithelial tumor cells of the invention may be administered to epithelial tissues of different sites, which include, but are not limited to epithelial tissues of cervical, vagina, oral cavity, esophagus, gastrointestinal epithelial tissues, and the like.

The percentages involved in the invention are all weight percentages, unless otherwise specified.

DETAILED DESCRIPTION OF INVENTION

It is shown in clinical studies that folic acid receptors are excessively expressed in the surface of most tumor cells, whereas are only present in few amount in normal cells. Therefore, folic acid and folic acid complexes (folic acid derivatives) can serve as tumor specific targeting molecule for diagnosis and treatment of tumors[4-5].

In the invention, the term "folic acid complex" is defined as a complex formed from the binding of the folic acid molecule to one or more other components, wherein the carboxylic group of the folic acid binds to the one or more other components by coupling or conjugation. The one or more other components may be, for example, drugs, radioactive nuclides, dyes, genes, developing agents, and the like. Examples of the folic acid complex are folic acid-mitomycin complex and folic acid-DTPA complex, and the like. In the composition and method of the invention, folic acid and/or folic acid complex may be administered simultaneously, or may be used alone. The folic acid complex used in the detecting agent composition described in the invention include folic acid conjugates formed by coupling of various small molecule compounds with folic acid, which include, but are not limited to folic acid-γ-cysteine, (R)-2-(2-(R)-3, 4-dihydroxy-5-carbonyl-2,5-dihydrofuran)-2-hydroxyethyl-4-(6-(2-amino-4-carbonyl-3,4-dihydropteridine)methylamino)benzoate, and the like.

The amount of folic acid in the composition of the invention is 0-5%, preferably 0-4.5%, 0-4%, 0-3.5%, 0-3%, 0-2.5%, 0-2%, 0-1.5%, even more preferably 0-1% by weight percentage. The amount of the folic acid complex in the composition of the invention is 0-10%, preferably 0-8%, 0-7%, 0-6%, 0-5%, 0-4%, 0-3%, 0-2%, even more preferably 0-1% by weight percentage.

Methylene blue is a clinically commonly used dye. Its mechanism of staining and color change is primarily based on its different colors in oxidation state and reduction state. Specifically, methylene blue in reduction state is colorless, whereas aqueous solution of methylene blue in oxidation state exhibits a blue color. Moreover, oxidized methylene blue, while present in the composition of the invention, may also exhibit a bluish green, blackish green (brownish green), and purple black color. The biological dye methylene blue has high affinity to cancer cells and melanin[7], whose oxidation and reduction property cause methylene blue to appear different color change spectra in the oxidation and reduction states of the tumor tissues. Such color changes can be directly identified by rapid visual observation.

The anti-oxidation capacity of tumor tissues is significantly enhanced as compared to normal tissues in general. However, significant oxidative stress still exists in such tumor issues[6]. Oxidative stress indicates oxidative lesion of the tissue, which is a period of occult pathological progression of the tissue. Although the reduction property of tumor cells is enhanced, their oxidation-reduction balance is still inclined to oxidation, unless the tumor cells are in an apoptotic or inhibited state. Therefore, in the intracellular environment of such vital cells, methylene blue in the composition of the invention is oxidized to exhibit the green, bluish green, blackish green and purple black color of the oxidation state.

In the composition of the invention, the folic acid complex and a few amount of folic acid can form a folic acid-methylene blue complex with methylene blue. Because the binding effect between the folic acid molecule and the folic acid receptor excessively expressed on the surface of the tumor cells, the folic acid-methylene blue complex can more easily enter into the cells with the promotion by acetic acid, and release methylene blue in reduction state. Furthermore, in tumor cells in oxidative stress, methylene blue is rapidly oxidized and thereby generates color change. With different malignant degree of the tumor, methylene blue turns into dark bluish green, blackish green, and purple black color, whereas in the presence of inflammatory lesion, cauliflower excrescence (HPV virus infection) or CIN I lesion, the color of methylene blue is green or light bluish green.

The "carbohydrate reducing agent" in the invention refers to any reductive carbohydrate, derivatives thereof, or combinations thereof. The carbohydrate includes, but is not limited to a monosaccharide, a disaccharide, or a polysaccharide. Specifically, the carbohydrate reductive agent can be glucose, fructose, galactose, hexose, lactose, maltose, and the like. The "carbohydrate derivative" described in the invention is defined as derivatives such as polysaccharide, glycoprotein, organic acid and the like formed by polymerization, esterification, oxidation and the like of carbohydrate substances. The amount of the carbohydrate reducing agent in the composition and method of the invention is 0.1-10%, preferably 0.3-8%, 0.1-3%, and 0.05-1%.

The carbohydrate reducing agent in the composition and method of the invention reduces the methylene blue in oxidation state to colorless methylene blue in reduction state. Folic acid and/or the folic acid complex bind to the folic acid receptor on the surface of the tumor cell. In an acidic environment of pH 5.0-5.5, folic acid and/or folic acid complex mediates the internalization and release of methylene blue in reductive state into the cytosol. Methylene blue in reductive state participates in the oxidative stress of the tumor tissues. The methylene blue in reductive state turns into the oxidative state. Meanwhile, the osmotic pressure of the intracellular fluid increases, causing the methylene blue in oxidative state to escape from the cells and immediately exhibit different color change. Such escaped methylene blue may adhere to the carrier for the administration of the invention, thereby immediately causing the composition on the carrier to exhibit color change. Specifically, the composition turns from light yellowish brown into dark bluish green, blackish green, and purple black color. Meanwhile, the tumor cells have enlarged nuclei and increased nuclear protein, which are precipitated and coagulated by acetic acid to produce a transient response, in which the abnormal epithelial tissue is shown as a acetowhite responsive region, which may provide location for the pathological sampling of the abnormal epithelial tissue.

The term "acetic acid" used in the invention is ethanoic acid. The composition of the invention comprises 2-6 w % acetic acid. The acetic acid used in the composition of the invention and the preparation method thereof provides an acidic pH, preferably pH 5.0-5.5. In addition, the use of acetic acid helps the composition of the invention to rapidly penetrate the cell, thereby interacting with the content of the cell so as to promote the occurrence of the color development. Moreover, as mentioned above, after methylene blue, which component is used to exhibit color change, escapes from the cell, the acetowhite response generated by acetic acid on the abnormal epithelial tissue further provides basis for the location of the abnormal epithelial tissue.

Cells that can be stained by the composition of the invention are tumor cells, preferably epithelial tumor cells. Said epithelial tissues include, but are not limited to cervical epithelium, vaginal epithelium, gastrointestinal epithelium, oral epithelium, and the like. Such cells may come from tissue biopsy samples.

The cells of the invention may be derived from mammalian subjects, said mammals include, but are not limited to human.

The invention is further illustrated in examples and comparative examples below. In the following examples and comparative examples, the cervical epithelial tissue is used as the object for inspection, and the pathological inspection results of cervical tissues are used as the standard for reference, the sensitivity is used to illustrate the detection rate of the detecting agent: the higher the sensitivity, the stronger the ability to find the abnormal epithelial tissue; and the specificity is used to illustrate the accuracy of the detecting agent: the higher the specificity, the higher the match between the detected abnormal epithelial tissue and the pathological inspection results.

In the invention, sensitivity and specificity are defined and calculated as follows:

Sensitivity=number of true positive/(number of true positive+number of false negative)*100%, Specificity=number of true negative/(number of true negative+number of false positive)*100%.

Example 1

Under normal temperature and pressure, each of the various components as specified in Table 1 below were individually dissolved in aqueous solvent, to which the biological detecting agent methylene blue were added, agitated and dissolved, followed by the addition of the reducing agent glucose and agitated for 30 minutes, then analytical pure acetic acid was added, agitated and mixed to make a detecting agent composition. The detecting agent composition was dipped with a large swab and smeared onto a cervical epithelial tissue. The swab was immediately taken out and immediate observed the color change of the swab. If the color of the swab was light yellowish brown, it indicated that there was no lesion of the epithelial tissue; if the color of the swab was light bluish green, it indicated inflammatory lesion, cauliflower excrescence (HPV virus infection) or CIN I lesion; if the color of the swab was dark bluish green, blackish green, and purple black, it indicated abnormal lesion of CIN II or higher. Meanwhile, colposcopy was recommended to take live tissues from multiple sites for histopathological examination, and then the sensitivity and the specificity of the detecting agent were tested using the histopathological testing results as the standard. The testing results are listed in Table 1.

Example 2

The method of Example 1 was repeated using the various components whose amounts were specified in the following Table 1, except that the folic acid complex folic acid γ-cysteine was used in place of folic acid. The testing results are listed in Table 1.

Example 3

The method of Example 1 was repeated using the various components whose amounts were specified in the following Table 1, except that folic acid and the folic acid complex (R)-2-(2-(R)-3,4-dihydroxy-5-carbonyl-2,5-dihydrofuran)-2-hydroxyethyl-4-(6-(2-amino-4-carbonyl-3,4-dihydropteridine)methylamino)benzoate were co-dissolved in the aqueous solvent. The testing results are listed in Table 1.

Example 4

The method of Example 1 was repeated using the various components whose amounts were specified in the following Table 1, except that folic acid and the folic acid complex (R)-2-(2-(R)-3,4-dihydroxy-5-carbonyl-2,5-dihydrofuran)-2-hydroxyethyl-4-(6-(2-amino-4-carbonyl-3,4-dihydropteridine)methylamino)benzoate were co-dissolved in the aqueous solvent, and the reducing agent, a hexose derivative was used in place of the reducing agent glucose. The testing results are listed in Table 1.

Comparative Example 1

Under normal temperature and pressure, 5 ml acetic acid was added into 95 ml distilled water for mixing to form a 5% acetic acid solution. The solution was dipped with a large cotton swab and smeared onto a cervical epithelial tissue. After waiting for one minute, the presence or absence of acetowhite region on the epithelial tissue was observed close to the boundary of the squamous column of the cervical, and its boundary, thickness, color and response time were observed. If there was an acetowhite region with clear boundary, it indicated lesion of CIN I or higher. Colposcopy was conducted to take live tissues from multiple sites for histopathological examination, and then the sensitivity and the specificity of the 5% acetic acid solution were tested using the histopathological testing results as the standard. The testing results are listed in Table 1.

Comparative Example 2

Under normal temperature and pressure, 10 g potassium iodide was dissolved into 100 ml distilled water, to which 5 g iodine was added, agitated and dissolved to make a Lugol's iodine solution. The solution was dipped with a large cotton swab and smeared onto a cervical epithelial tissue to observe whether the epithelial tissue was stained by iodine. Normal epithelium exhibited reddish brown or black color, whereas abnormal epithelium exhibited thick mustard yellow or yellowish brown color. Colposcopy was conducted to take live tissues from multiple sites for histopathological examination, and then the sensitivity and the specificity of the Lugol's iodine solution were tested using the histopathological testing results as the standard. The testing results are listed in Table 1.

TABLE 1

Performance and amount of various components (weight percentage)

| | Example 1 | Example 2 | Example 3 | Example 4 | Comparative Example 1 | Comparative Example 2 |
|---|---|---|---|---|---|---|
| Folic acid | 1 | / | 1 | 1 | / | / |
| Folic acid complex | / | 1.0 | 0.5 | 0.5 | / | / |
| Methylene blue | 0.3 | 0.3 | 0.3 | 0.3 | / | / |
| Glucose | 1.0 | 0.5 | 0.5 | / | / | / |
| Hexose derivative | / | / | / | 1.0 | / | / |
| Acetic acid | 5 | 5 | 5 | 5 | 5.2 | / |
| Distilled water | 5 | 5 | 3 | 3 | 94.8 | 87 |
| Potassium iodide | / | / | / | / | / | 8.7 |
| Iodine | / | / | / | / | / | 4.3 |
| Sensitivity (Percentage) | 94.1 | 94.7 | 97.9 | 95.8 | 65.7 | 58.5 |
| Specificity (Percentage) | 92.6 | 90.5 | 95.3 | 94.6 | 54.9 | 50.2 |

From the aforesaid Table 1 it can be seen that the examples using the detecting agent composition of the present invention all have significant advantages in sensitivity and specificity as compared to the detecting agents in the comparative examples, indicating that the composition of the invention can be sensitively and specifically used for detecting abnormal epithelial tissue.

REFERENCE

1. Qiao Youlin, Zhang Wenhua, Zhao Fanghui, Pan Qinjing, Li Ling, "Screen, Early Diagnosis, and Early Treatment Solutions for Cervical Cancer", July, 2003;
2. Mashberg, A: J. Amer. Dent. Assoc, 1983. 106-112;
3. Canto M I, Setrakian S, Willis J, et al, Methylene blue-directed biopsies improve detection intestinal metaplasia and dysplasia in Barrett's esophagus [J]. Gastrointest Endosc, 2000, 5:560;
4. Zhao X B, Lee R J. Tumor-selective targeted delivery of genes and antisen seo ligo deoxyribonuc leo tides via the folate receptor [J]. Adv Drug Deliv Rev, 2004, 56(8): 191-193;
5. Reddy J A, Allagadda V m, Leamon C P. Targeting therapeutic and imaging agents to folate receptor positive tumors [J]. Current Pham Biotech, 2005, 6, 131-150;
6. Wu Chenheng, "Oxidative and Reductive States of Malignant Tumor Tissues: First Exploration of the Relation between Change of Antioxidation Capacity and Apoptosis and Mechanism Therefore", Apr. 26, 2005;
7. Link E M, Blower P J, Costa D C, et al, Early detection of melanoma metastases with radioiodinated methylene blue [J]. Eur J Nuclear Med, 1998, 25 (9):1322.
8. Leamon C P, Deprince R B, Hendren R W. Folate-mediated drug delivery: effect of alternative conjugation chemistry [J]. Drug Target, 1999, 7:157-169.
9. Leamon C P, Cooper S R, Hardee G E. Folate-liposome-mediated antisense oligodeoxynucleotide targeting to cancer cells: evaluation in vitro and vivo [J]. Bioconjug Chem, 2003, 14:738-747.

The invention claimed is:
1. A detecting agent composition comprising methylene blue, carbohydrate reducing agent, acetic acid, water, and folic acid complex,
   wherein a weight percentage of the folic acid complex is up to 10%,
   a weight percentage of the methylene blue is 0.01-5%,
   a weight percentage of the carbohydrate reducing agent is 0.1-10%,
   a weight percentage of the acetic acid is 2-6%,
   a weight percentage of the water is 3-95%,
   the weight percentage of the folic acid complex is not 0%,
   wherein the folic acid complex is (R)-2-(2-(R)-3,4-dihydroxy-5-carbonyl-2,5-dihydrofuran)-2-hydroxyethyl-4-(6-(2-amino-4-carbonyl-3,4-dihydropteridine)methylamino)benzoate, and
   wherein the detecting agent composition has an acidic pH below 5.5.
2. The detecting agent composition according to claim 1, wherein the weight percentage of the folic acid complex is up to 8%; and/or wherein the weight percentage of the methylene blue is 0.05-4.5%; and/or wherein the carbohydrate reducing agent is selected from carbohydrates or derivatives thereof.
3. The detecting agent composition according to claim 1, wherein the weight percentage of the acetic acid is 3-5%.
4. The detecting agent composition according to claim 1, wherein the detecting agent composition is a detecting agent composition for epithelial tumor cells.
5. A method for preparing a detecting agent composition including methylene blue, carbohydrate reducing agent, acetic acid, water, and folic acid complex comprising the steps of:
   (a) dissolving the folic acid complex into an aqueous solvent,

(b) adding, agitating and dissolving the methylene blue into the solvent, (c) adding the carbohydrate reducing agent into the solvent, (d) agitating the solvent for 30 minutes, and (e) adding the acetic acid for agitation, wherein the steps (a)-(e) are all conducted under normal temperature and pressure, wherein in the detecting agent composition,
a weight percentage of the folic acid complex is up to 10%,
a weight percentage of the methylene blue is 0.01-5%,
a weight percentage of the carbohydrate reducing agent is 0.1-10%,
a weight percentage of the acetic acid is 2-6%,
a weight percentage of the water is 3-95%, and
the weight percentage of the folic acid complex is not 0%, wherein the folic acid complex is (R)-2-(2-(R)-3,4-dihydroxy-5-carbonyl-2,5-dihydrofuran)-2-hydroxyethyl-4-(6-(2-amino-4-carbonyl-3,4-dihydropteridine)methylamino)benzoate, and wherein the detecting agent composition has an acidic pH below 5.5.

6. A kit for detecting epithelial tumor cells comprising the detecting agent composition according to claim 1, and a carrier.

7. The detecting agent composition according to claim 2, wherein the weight percentage of the acetic acid is 3-5%.

8. The detecting agent composition according to claim 2, wherein the detecting agent composition is a detecting agent composition for epithelial tumor cells.

9. The method according to claim 5, wherein in the detecting agent composition, the weight percentage of the folic acid complex is up to 8%; and/or wherein the weight percentage of the methylene blue is 0.05-4.5%; and/or wherein the carbohydrate reducing agent is selected from carbohydrates or derivatives thereof.

10. The method according to claim 5, wherein the weight percentage of the acetic acid is 3-5%.

11. The method according to claim 5, wherein the detecting agent composition is a detecting agent composition for epithelial tumor cells.

12. The kit according to claim 6, wherein in the detecting agent composition, the weight percentage of the folic acid complex is up to 8%; and/or wherein the weight percentage of the methylene blue is 0.05-4.5%; and/or wherein the carbohydrate reducing agent is selected from carbohydrates or derivatives thereof.

13. The kit according to claim 6, wherein the weight percentage of the acetic acid is 3-5%.

14. The kit according to claim 6, wherein the detecting agent composition is a detecting agent composition for epithelial tumor cells.

15. The method according to claim 9, wherein the weight percentage of the acetic acid is 3-5%.

16. The method according to claim 9, wherein the detecting agent composition is a detecting agent composition for epithelial tumor cells.

17. The kit according to claim 12, wherein the weight percentage of the acetic acid is 3-5%.

18. The kit according to claim 12, wherein the detecting agent composition is a detecting agent composition for epithelial tumor cells.

19. The detecting agent composition according to claim 2, wherein the weight percentage of the folic acid complex is up to 1%.

20. The detecting agent composition according to claim 2, wherein the weight percentage of the methylene blue is 0.05-0.5%.

21. The detecting agent composition according to claim 2, wherein the carbohydrate reducing agent is selected from glucose, fructose, galactose, hexose, lactose, maltose, or derivatives thereof.

22. The kit according to claim 6, wherein the carrier is selected from absorbent cotton swabs, gauze, microcapsules, cellulose membranes, filter paper, nanomaterials, or aerogel.

23. The method according to claim 9, wherein the weight percentage of the folic acid complex is up to 1%.

24. The method according to claim 9, wherein the weight percentage of the methylene blue is 0.05-0.5%.

25. The method according to claim 9, wherein the carbohydrate reducing agent is selected from glucose, fructose, galactose, hexose, lactose, maltose, or derivatives thereof.

26. The kit according to claim 12, wherein the weight percentage of the folic acid complex is up to 1%.

27. The kit according to claim 12, wherein the weight percentage of the methylene blue is 0.05-0.5%.

28. The kit according to claim 12, wherein the carbohydrate reducing agent is selected from glucose, fructose, galactose, hexose, lactose, maltose, or derivatives thereof.

* * * * *